United States Patent [19]  [11] 3,980,777
Hoffmann et al.  [45] Sept. 14, 1976

[54] O-ALKYL-O-[2-ALKYLTHIO-IMIDAZOL(4)YL](THIONO)-PHOSPHORIC(PHOSPHONIC) ACID ESTERS AND ESTER-AMIDES

[75] Inventors: Hellmut Hoffmann, Wuppertal; Ingeborg Hammann, Cologne; Bernhard Homeyer, Opladen, all of Germany

[73] Assignee: Bayer Aktiengesellschaft, Leverkusen, Germany

[22] Filed: June 20, 1975

[21] Appl. No.: 588,922

[30] Foreign Application Priority Data
July 2, 1974  Germany............................ 2431848

[52] U.S. Cl.................................. 424/200; 260/309
[51] Int. Cl.$^2$............................................. C07F 9/65
[58] Field of Search....................... 260/309; 424/200

[56] References Cited
UNITED STATES PATENTS

| | | | |
|---|---|---|---|
| 3,150,149 | 9/1964 | Uhlenbroek et al. | 260/310 R |
| 3,185,699 | 5/1965 | Sherlock | 260/310 R |
| 3,216,894 | 11/1965 | Lorenz et al. | 260/309 |
| 3,232,830 | 2/1966 | Schrader et al. | 260/310 R |
| 3,728,297 | 4/1973 | Hoffmann et al. | 260/310 R |
| 3,818,030 | 6/1974 | Timmler et al. | 260/309 |
| 3,839,355 | 10/1974 | Hoffmann et al. | 260/310 R |

Primary Examiner—Natalie Trousof
Attorney, Agent, or Firm—Burgess, Dinklage & Sprung

[57] ABSTRACT

O-Alkyl-O-[2-alkylthio-imidazo(4)yl]-(thiono)-phosphoric (phosphonic) acid esters and ester-amides of the formula

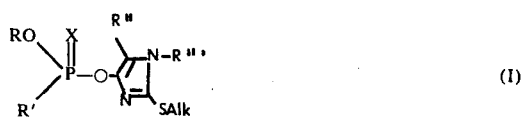

in which
R is alkyl with 1 to 6 carbon atoms,
R' is alkyl, alkoxy or mono- or dialkylamino with 1 to 6 carbon atoms in each alkyl moiety,
R'' is cyano or carbalkoxy with 1 to 5 carbon atoms in the alkyl chain,
R''' is alkyl or alkenyl with up to 6 carbon atoms,
Alk is alkyl with 1 to 5 carbon atoms, and
X is oxygen or sulfur,
which possess insectical, acaricidal and nematicidal properties.

10 Claims, No Drawings

O-ALKYL-O-[2-ALKYLTHIO-IMIDAZOL(-4)YL](THIONO)-PHOSPHORIC(PHOSPHONIC) ACID ESTERS AND ESTER-AMIDES

The present invention relates to and has for its objects the provisions of particular new O-alkyl-O-[2-alkylthioimidazol(4)yl]-(thiono)-phosphoric(phosphonic) acid esters and ester-amides, i.e. O,O-dialkyl-O-[1-alkyl- or -alkenyl- 2-alkylthio-5-cyano- or -carbalkoxy- imidazol(4)yl]-phosphoric acid esters, their alkanephosphonic acid esters, thiono and/or ester-amide counterparts, which possess insecticidal, acaricidal and nematicidal properties, active compositions in the form of mixtures of such compounds with solid and liquid dispersible carrier vehicles, and methods for producing such compounds and for using such compounds in a new way especially for combating pests, e.g. insects, acarids and nematodes, with other and further objects becoming apparent from a study of the within specification and accompanying examples.

It is known from U.S. Pat. No. 3,843,679 that pyrazolylthionophosphoric acid esters, for example O,O-dimethyl- (Compound A) and O,O-diethyl-O-[1-methyl-3-carboethoxy-pyrazol(5)yl]- (Compound B) or -O-[1-methyl-3-carbomethoxy-pyrazol(5)yl]-thionophosphoric acid ester (Compounds C and D) possess insecticidal and acaricidal properties.

The present invention provides, as new compounds, the imidazolyl-(thiono)-phosphoric(phosphonic) acid esters and ester-amides of the general formula

in which
R is alkyl with 1 to 6 carbon atoms,
R' is alkyl, alkoxy or mono- or dialkylamino with 1 to 6 carbon atoms in each alkyl moiety,
R'' is cyano or carbalkoxy with 1 to 5 carbon atoms in the alkyl chain,
R''' is alkyl or alkenyl with up to 6 carbon atoms,
Alk is alkyl with 1 to 5 carbon atoms, and
X is oxygen or sulfur.

Preferably R is straight-chain or branched alkyl with 1 to 4 (especially 1 to 3) carbon atoms, R' is straight-chain or branched alkyl or alkoxy with in either case 1 to 4 (especially 1 to 3) carbon atoms, or monoalkylamino or dialkylamino with 1 to 5 (especially 1 to 4) carbon atoms per alkyl chain, R'' is cyano or carbalkoxy with 1 to 4 (especially 1 to 3) carbon atoms in the alkoxy radical, R''' is straight-chain or branched alkyl with 1 to 5 (especially 1 to 4) carbon atoms, or alkenyl with 2 to 5 (especially 3 or 4) carbon atoms, and Alk is straight-chain or branched alkyl with 1 to 4 (especially 1 to 3) carbon atoms.

Surprisingly, the imidazolyl(thiono)-phosphoric(phosphonic) acid esters and ester-amides according to the invention possess a better insecticidal, including soil-insecticidal, acaricidal and nematicidal action than the previously known compounds of analogous structure and of the same type of action. The compounds according to the invention thus represent a genuine enrichment of the art.

The present invention also provides a process for the preparation of an imidazolyl-(thiono)-phosphoric(phosphonic) acid ester or ester-amide of the formula (I), in which a (thiono)phosphoric(phosphonic) acid ester halide or ester-amide halide of the general formula

in which
R, R' and X have the above-mentioned meanings and
Hal is halogen, is reacted, optionally in the presence of a diluent or solvent, with a 2-alkylthio-4-hydroxy-imidazole derivative of the general formula

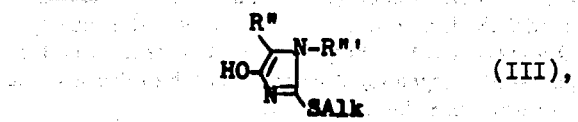

in which
R'', R''' and Alk have the above-mentioned meanings, the imidazole derivative being reacted as such, in the presence of an acid acceptor or, in the form of an alkali metal salt, alkaline earth metal salt or ammonium salt thereof.

If, for example, O-ethyl-O-sec.-butyl-thionophosphoric acid chloride and 1-allyl-2-n-propylthio-4-hydroxy-5-cyanoimidazole are used as starting materials, the course of the reaction can be represented by the following equation:

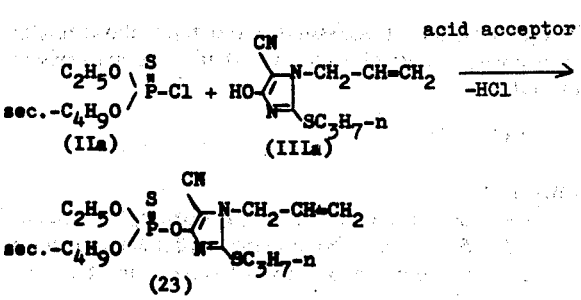

The (thiono)phosphoric(phosphonic) acid ester halides and ester-amide halides (II) to be used as starting materials are known from the literature and can be prepared according to generally customary processes.

The following may be mentioned as examples thereof: O,O-dimethyl-, O,O-diethyl-, O,O-di-n-propyl-, O,O-di-isopropyl-, O,O-di-n-butyl-, O,O-di-isobutyl-, O,O-di-sec.-butyl-, O,O-di-tert.-butyl-, O-ethyl-O-n-propyl-, O-ethyl-O-isopropyl-, O-n-butyl-O-ethyl-, O-ethyl-O-sec.-butyl- and O-ethyl-O-methyl-phosphoric acid diester chlorides and the corresponding thiono analogues; O-methyl-, O-ethyl-, O-n-propyl-, O-isopropyl-, O-n-butyl-, O-sec.-butyl-, O-isobutyl- and O-tert.-butyl-methane-, -ethane-, -n-propane-, -isopropane-, -n-butane-, -isobutane-, -sec.-butane- and -tert.-butane-phosphonic acid ester chlorides and the corresponding thiono analogues; and O-methyl-N-methyl-, O-ethyl-N-methyl-, O-n-propyl-N-methyl-, O-isopropyl-N-methyl-, O-n-butyl-N-methyl-, O-sec.-butyl-N-methyl-, O-methyl-N-ethyl-, O-ethyl-N-ethyl-, O-n-propyl-N-ethyl-, O-isopropyl-N-ethyl-, O-n-butyl-N-ethyl-, O-sec.-butyl-N-ethyl-, O-methyl-N-n-propyl-, O-ethyl-N-n-propyl-, O-n-propyl-N-n-propyl-, O-n-propyl-N-n-butyl-, O-isopropyl-N-n-propyl, O-isopropyl-N-n-butyl-, O-tert.-butyl-N-ethyl-, O-ethyl-N-pentyl-, O-n-propyl-N-pentyl-, O-isopropyl-N-pentyl-, O-n-butyl-N-pentyl-, O-sec.-butyl-N-pentyl-, O-tert.-butyl-N-pentyl-, O-methyl-N,N-dimethyl-, O-methyl-N,N-diethyl-, O-methyl-N,N-di-n-propyl-, O-methyl-N,N-di-isopropyl-, O-ethyl-N,N-dimethyl-, O-ethyl-N,N-diethyl-, O-ethyl-N,N-di-n-propyl-, O-ethyl-N,N-di-isopropyl-, O-ethyl-N,N-di-n-butyl-, O-ethyl-N,N-di-n-pentyl-, O-n-propyl-N,N-dimethyl-, O-n-propyl-N,N-diethyl-, O-n-propyl-N,N-di-n-propyl-, O-n-propyl-N,N-di-isopropyl-, O-n-propyl-N,N-di-n-butyl-, O-N-propyl-N,N-di-n-pentyl-, O-n-butyl-N,N-dimethyl-, O-n-butyl-N,N-diethyl-, O-n-butyl-N,N-di-n-propyl-, O-n-butyl-N,N-di-isopropyl-, O-n-butyl-N,N-di-n-butyl- and O-n-butyl-N,N-di-n-pentyl-phosphoric acid ester-amide chlorides and the corresponding thiono analogues.

The 2-alkylthio-4-hydroxy-imidazole derivatives (III), some of which have not yet been described in the literature, can be prepared according to processes known from the literature, namely, in the case where R'' is cyano, by a. reacting the known aminoacetonitriles of the general formula

in which
R''' has the above-mentioned meaning, with carbonic acid ethyl ester isothiocyanate of the formula $$C_2H_5O-CO-NCS \qquad (V)$$

in the presence of alcoholate, and then allowing the intermediate product to react with a compound of the formula AlkZ wherein
Z is an easily removed radical, for example halogen, and Alk has the above-mentioned meaning, with renewed addition of alcoholate, or, in the case where
R'' represents carboalkoxy, by
b. reacting potassium thiocyanate, chlorocarbonic acid ethyl ester and aminoacetic acid ester derivatives of the general formula $$R'''-HN-CH_2-CO_2-R^{IV} \qquad (VI)$$

to give intermediate products of the general formula

in which last-mentioned formulas
R''' has the above-mentioned meaning and
$R^{IV}$ is alkyl with 1 to 5 carbon atoms,
then cyclizing these intermediate products and reacting them, for example in accordance with the equation given below, as described under (a), with a compound of the formula AlkZ wherein
Z is an easily removed radical, for example halogen, and
Alk has the above-mentioned meaning:

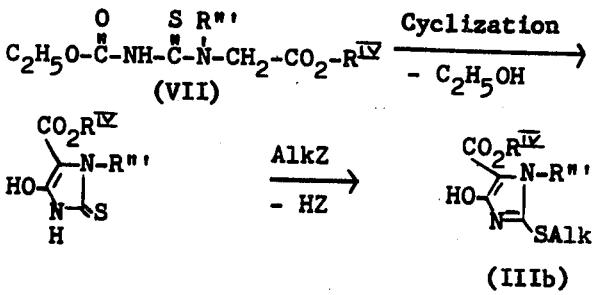

The following may be mentioned as examples of 2-alkylthio-4-hydroxy-imidazole derivatives (III) to be reacted in accordance with the process: 1-methyl-, 1-ethyl-, 1-n-propyl-, 1-isopropyl-, 1-n-butyl-, 1-sec.-butyl-, 1-isobutyl-, 1-tert.-butyl-, 1-n-pentyl-, 1-allyl-, 1-buten-2'-yl- and 1-buten-3'-yl-2-methylthio-, -2-ethylthio-, -2-n-propylthio-, -2-isopropylthio-, -2-butylthio-, -2-sec.-butylthio-, -2-isobutylthio- and -2-tert.-butylthio-4-hydroxy-5-cyanoimidazole, as well as the corresponding 5-carbomethoxy, 5-carbethoxy, 5-carbo-n-propoxy, 5-carbo-isopropoxy, 5-carbo-n-butoxy, 5-carbo-isobutoxy and 5-carbo-tert.-butoxy derivatives.

The process for the preparation of the compounds according to the invention is preferably carried out in the presence of a suitable solvent or diluent. Practically all inert organic solvents can be used for this purpose, especially aliphatic and aromatic, optionally chlorinated hydrocarbons, such as benzene, toluene, xylene, benzine, methylene chloride, chloroform, carbon tetrachloride and chlorobenzene; ethers, for example diethyl ether, dibutyl ether and dioxane; ketones, for example acetone, methyl ethyl ketone, methyl isopropyl ketone and methyl isobutyl ketone; and nitriles, such as acetonitrile and propionitrile.

All customary acid-binding agents can be used as acid acceptors. Alkali metal carbonates and alkali metal alcoholates, such as sodium carbonate and potassium carbonate, sodium methylate and ethylate and potassium methylate and ethylate, have proved particularly suitable, as have aliphatic, aromatic or heterocyclic amines, for example triethylamine, dimethylamine, dimethylaniline, dimethylbenzylamine and pyridine.

The reaction temperature can be varied within a fairly wide range. In general, the reaction is carried out at between 0° and 120°C, preferably at from 60° to 80°C.

The reaction is in general allowed to take place under normal pressure.

To carry out the process of this invention, the starting materials are in general employed in equimolar amounts. An excess of one or other component in general results in no significant advantages. The reaction is preferably carried out in the presence of one of the above-mentioned solvents, if appropriate in the presence of an acid acceptor, at the temperatures indicated. After a reaction time of from one to several hours, in most cases at elevated temperatures, the reaction mixture is cooled and poured into water, and the reaction mixture is extracted by shaking with an organic solvent, for example methylene chloride, and is worked up in the usual manner by washing and drying the organic phase and distilling off the solvent.

The new compounds are frequently obtained in the form of oils which in most cases cannot be distilled without decomposition, but are freed from the last volatile constituents by so-called "slight distillation", that is to say by prolonged heating under reduced pressure to moderately elevated temperatures, and are purified in this way. They are characterized by the refractive index. Some compounds are obtained in a crystalline form and have a sharp melting point.

As has already been mentioned, the imidazolyl-(thiono)phosphoric(phosphonic) acid esters and ester-amides according to the invention are distinguished by an excellent insecticidal, including soil-insecticidal, acaricidal and nematicidal activity. They are active against plant pests, pests harmful to health and pests of stored products. They combine a low phytotoxicity with a good action against both sucking and biting insects and against mites.

For this reason, the compounds according to the invention can be employed successfully as pesticides in plant protection and in the hygiene field and the field of protection of stored products.

To the sucking insects there belong, in the main, aphids (Aphididae) such as the green peach aphid (*Myzus persicae*), the bean aphid (*Doralis fabae*), the bird cherry aphid (*Rhopalosiphum padi*), the pea aphid (*Macrosiphum pisi*) and the potato aphid (*Macrosiphum solanifolii*), the currant gall aphid (*Cryptomyzus korschelti*), the rosy apple aphid (*Sappaphis mali*), the mealy plum aphid (*Hyalopterus arundinis*) and the cherry black-fly (*Myzus cerasi*); in addition, scales and mealybugs (Coccina), for example the oleander scale (*Aspidiotus hederae*) and the soft scale (*Lecanium hesperidum*) as well as the grape mealybug (*Pseudococcus maritimus*); thrips (Thysanoptera), such as *Hercinothrips femoralis*, and bugs, for example the beet bug (*Piesma quadrata*), the red cotton bug (*Dysdercus intermedius*), the bed bug (*Climex lectularius*), the assassin bug (*Rhodnius prolixus*) and Chagas' bug (*Triatoma infestans*) and, further, cicadas, such as *Euscelis bilobatus* and *Nephotettix bipunctatus*.

In the case of the biting insects, above all there should be mentioned butterfly caterpillars (Lepidoptera) such as the diamond-back moth (*Plutella maculipennis*), the gypsy moth (*Lymantria dispar*), the brown-tail moth (*Euproctis chrysorrhoea*) and tent caterpillar (*Malacosoma neustria*), further, the cabbage moth (*Mamestra brassicae*) and the cutworm (*Agrotis segetum*), the large white butterfly (*Pieris brassicae*), the small winter moth (*Cheimatobia brumata*), the green oak tortrix moth (*Tortrix viridana*), the fall armyworm (*Laphygma frugiperda*) and cotton worm (*Prodenia litura*), the ermine moth (*Hyponomeuta padella*), the Mediterranean flour moth (*Ephestia kuehniella*) and greater wax moth (*Galleria mellonella*).

Also to be classed with the biting insects are beetles (Coleoptera), for example the granary weevil (*Sitophilus granarius* = Calandra granaria), the Colorado beetle (*Leptinotarsa decemlineata*), the dock beetle (*Gastrophysa viridula*), the mustard beetle (*Phaedon cochleariae*), the blossom beetle (*Meligethes aeneus*), the raspberry beetle (*Byturus tomentosus*), the bean weevil (*Bruchidius* = *Acanthoscelides obtectus*), the leather beetle (*Dermestes frischi*), the khapra beetle (*Trogoderma granarium*), the flour beetle (*Tribolium castaneum*), the northern corn billbug (Calandra or *Sitophilus zeamais*), the drugstore beetle (*Stegobium paniceum*), the yellow mealworm (*Tenebrio molitor*) and the saw-toothed grain beetle (*Oryzaephilus surinamensis*), and also species living in the soil, for example wireworms (*Agriotes spec.*) and larvae of the cockchafer (*Melolontha melolontha*); cockroaches, such as the German cockroach (*Blattella germanica*), American cockroach (*Periplaneta americana*), Madeira cockroach (Leucophaea or *Rhyparobia maderae*), oriental cockroach (*Blatta orientalis*), the giant cockroach (*Blaberus giganteus*) and the black giant cockroach (*Blaberus fuscus*) as well as (*Henschoutedenia flexivitta*; further, Orthoptera, for example the house cricket (*Gryllus domesticus*); termites such as the eastern subterranean termite (*Reticulitermes flavipes*) and Hymenoptera such as ants, for example the garden ant (*Lasius niger*).

The Diptera comprise essentially the flies, such as the vinegar fly (*Drosophila melanogaster*), the Mediterranean fruit fly (*Ceratitis capitata*), the house fly (*Musca domestica*), the little house fly (*Fannia canicularis*), the black blow fly (*Phormia regina*) and bluebottle fly (*Calliphora erythrocephala*) as well as the stable fly (*Stomoxys calcitrans*); further, gnats, for example mosquitoes such as the yellow fever mosquito (*Aedes aegypti*), the northern house mosquito (*Culex pipiens*) and the malaria mosquito (*Anopheles stephensi*).

With the mites (Acarina) there are included, in particular, the spider mites (Tetranychidae) such as the two-spotted spider mite (*Tetranychus urticae*) and the European red mite (*Paratetranychus pilosus* = *Panonychus ulmi*), gall mites, for example the blackcurrant gall mite (*Eriophyes ribis*) and tarsonemids, for example the broad mite (*Hemitarsonemus latus*) and the cyclamen mite (*Tarsonemus pallidus*); finally, ticks, such as the relapsing fever tick (*Ornithodorus moubata*).

The active compounds according to the invention couple a low toxicity to warm-blooded animals with powerful nematicidal properties and can therefore be used to combat nematodes, especially phytopathogenic nematodes. These essentially include leaf nematodes (Arphelenchoides), such as the chrysanthemum eelworm (*A. ritzemabosi*), the leaf-blotch eelworm (*A. fragariae*) and the rice eelworm (*A. oryzae*); stem nematodes (Ditylenchus), such as the stem eelworm (*D.Dipsaci*); root-knot nematodes (Meloidogyne), such as *M. arenaria* and *M. incognita*; cyst-forming nematodes (Heterodera), such as the potato cyst eelworm (*H. rostochiensis*) and the beet cyst eelworm (*H. schachtii*); and also free-living root nematodes, for example of the genera Pratylenchus, Paratylenchus, Rotylenchus, Xiphinema and Radopholus.

When applied against pests harmful to health and pests of stored products, particularly flies and mosquitoes, the present compounds are also distinguished by an outstanding residual activity on wood and clay, as well as a good stability to alkali on limed substrates.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other insecticides, acaricides and nematicides, or fungicides, bactericides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001-10%, preferably 0.01–1%, by weight of the mixture. Thus, the present invention contemplates over-all compositions which comprise mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

When used against nematodes, the preparations are generally applied to an area of agriculture in amounts of 1 to 100 kg of active compound per hectare, and are then incorporated into the soil.

Furthermore, the present invention contamplates methods of selectively killing, combating or controlling pests, e.g. insects, acarids and nematodes, which comprises applying to at least one of correspondingly (a) such insects, (b) such acarids, (c) such nematodes, and (d) the corresponding habitat thereof, i.e. the locus to be protected, e.g. to a growing crop, to an area where a crop is to be grown or to a domestic animal, a correspondingly combative or toxic amount, i.e. an insecticidally, acaricidally or nematicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

Plutella test

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dew moist and were then infested with caterpillars of the diamond-back moth (*Plutella maculipennis*).

After the specified periods of time, the degree of destruction was determined as a percentage: 100% means that all the caterpillars were killed whereas 0% means that none of the caterpillars were killed.

The active compounds, the concentrations of the active compounds, the evaluation times and the results can be seen from the following table:

Table 1

| Active compound | (Plutella test) Active compound concentration in % | Degree of destruction % after 3 days |
| --- | --- | --- |
| 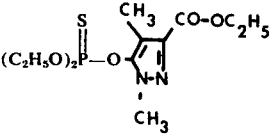 (E) | 0.1<br>0.01 | 100<br>0 |
| 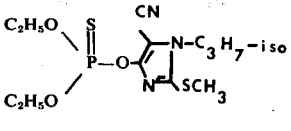 (1) | 0.01 | 100 |
| 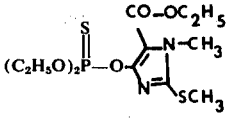 (2) | 0.01 | 100 |
| 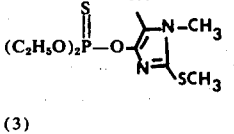 (3) | 0.01 | 100 |
| 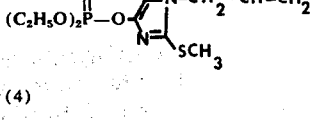 (4) | 0.01 | 100 |
| 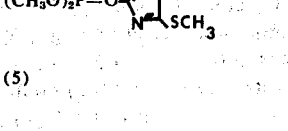 (5) | 0.01 | 100 |
| 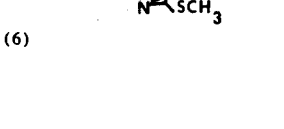 (6) | 0.01 | 100 |

Table 1-continued (Plutella test)

| Active compound | Active compound concentration in % | Degree of destruction % after 3 days |
|---|---|---|
| (7) $C_2H_5O$–P(=S)($C_2H_5$)–O–[ring: CN, N–$C_3H_7$-iso, N=, $SCH_3$] | 0.01 | 100 |
| (8) $C_2H_5O$–P(=O)($C_2H_5$)–O–[ring: CN, N–$C_2H_5$, N=, $SCH_3$] | 0.01 | 100 |
| (9) $(C_2H_5O)_2$P(=S)–O–[ring: CN, N–$C_2H_5$, N=, $SCH_3$] | 0.01 | 100 |
| (14) $C_2H_5O$–P(=O)($C_2H_5$)–O–[ring: CN, N–$CH_3$, N=, $SCH_3$] | 0.01 | 100 |
| (17) $(CH_3O)_2$P(=S)–O–[ring: $CO$–$OC_2H_5$, N–$C_3H_7$-iso, N=, $SC_2H_5$] | 0.01 | 100 |

EXAMPLE 2

Myzus test (contact action)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were sprayed with the preparation of the active compound until dripping wet.

After the specified periods of time, the degree of destruction was determined as a percentage: 100% means that all the aphids were killed whereas 0% means that none of the aphids were killed.

The active compounds, the concentrations of the active compounds, the evaluation times and the results can be seen from the following table:

Table 2
(Myzus test)
| Active compound | Active compound concentration in % | Degree of destruction in % after 1 day |
|---|---|---|
| 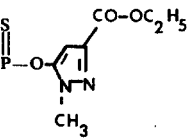 (A) | 0.01<br>0.001 | 98<br>0 |
| 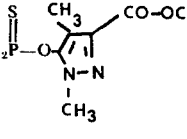 (E) | 0.01<br>0.001 | 100<br>0 |
| 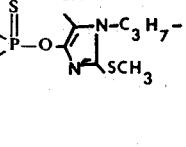 (1) | 0.01<br>0.001 | 100<br>100 |
| 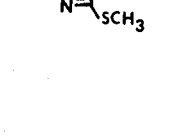 (3) | 0.01<br>0.001 | 100<br>100 |
| 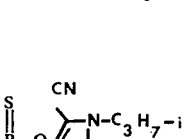 (4) | 0.01<br>0.001 | 100<br>100 |
| 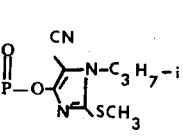 (5) | 0.01<br>0.001 | 100<br>99 |
| 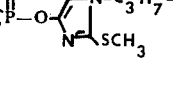 (6) | 0.01<br>0.001 | 100<br>99 |
|  (7) | 0.01<br>0.001 | 100<br>99 |

Table 2-continued

| Active compound | (Myzus test) Active compound concentration in % | Degree of destruction in % after 1 day |
|---|---|---|
| 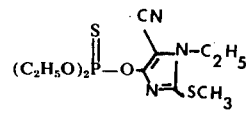 (9) | 0.01 0.001 | 100 100 |
| 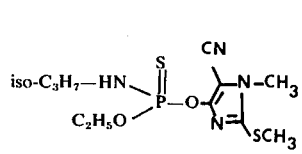 (12) | 0.01 0.001 | 100 95 |

EXAMPLE 3

Tetranychus test (resistant)

Solvent: 3 parts by weight of acetone
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Bean plants (*Phaseolus vulgaris*), which had a height of approximately 10–30 cm, were sprayed with the preparation of the active compound until dripping wet. These bean plants were heavily infested with the two-spotted spider mite (*Tetranychus urticae*) in all stages of development.

After the specified periods of time, the degree of destruction was determined as a percentage: 100% means that all the spider mites were killed, whereas 9% means that none of the spider mites were killed.

The active compounds, the concentrations of the active compounds, the evaluation times and the results can be seen from the following table:

Table 3

| | Active compound | (Tetranychus test) Active compound concentration in % | Degree of destruction in % after 2 days |
|---|---|---|---|
| (A) | 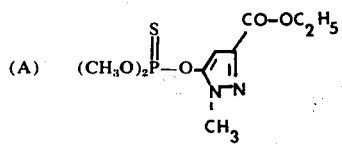 | 0.1 | 0 |
| (B) | 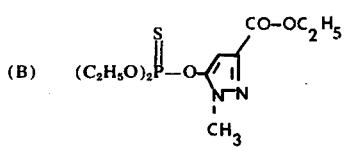 | 0.1 0.01 | 20 0 |
| (C) | 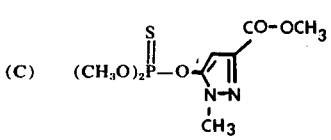 | 0.1 | 0 |

Table 3-continued (Tetranychus test)

| | Active compound | Active compound concentration in % | Degree of destruction in % after 2 days |
|---|---|---|---|
| (D) | $(C_2H_5O)_2\overset{S}{P}-O-$ pyrazole with $CO-OCH_3$, $N-N$, $CH_3$ | 0.1<br>0.01 | 20<br>0 |
| (E) | $(C_2H_5O)_2\overset{S}{P}-O-$ pyrazole with $CH_3$, $CO-OC_2H_5$, $N-N$, $CH_3$ | 0.1 | 0 |
| (1) | $\begin{matrix}C_2H_5O\\C_2H_5O\end{matrix}\overset{S}{P}-O-$ ring with $CN$, $N-C_3H_7-iso$, $SCH_3$ | 0.1<br>0.01 | 100<br>95 |
| (3) | $(C_2H_5O)_2\overset{S}{P}-O-$ ring with $CN$, $N-CH_3$, $SCH_3$ | 0.1<br>0.01 | 100<br>98 |
| (4) | $(C_2H_5O)_2\overset{S}{P}-O-$ ring with $CN$, $N-CH_2-CH=CH_2$, $SCH_3$ | 0.1<br>0.01 | 100<br>100 |
| (5) | $(CH_3O)_2\overset{S}{P}-O-$ ring with $CN$, $N-C_3H_7-iso$, $SCH_3$ | 0.1 | 98 |
| (6) | $(C_2H_5O)_2\overset{O}{P}-O-$ ring with $CN$, $N-C_3H_7-iso$, $SCH_3$ | 0.1 | 100 |
| (7) | $\begin{matrix}C_2H_5O\\C_2H_5\end{matrix}\overset{S}{P}-O-$ ring with $CN$, $N-C_3H_7-iso$, $SCH_3$ | 0.1<br>0.01 | 100<br>99 |
| (8) | $\begin{matrix}C_2H_5O\\C_2H_5\end{matrix}\overset{O}{P}-O-$ ring with $CN$, $N-C_2H_5$, $SCH_3$ | 0.1 | 99 |

Table 3-continued
(Tetranychus test)

| Active compound | | Active compound concentration in % | Degree of destruction in % after 2 days |
|---|---|---|---|
| (9) | 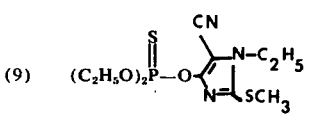 | 0.1<br>0.01 | 100<br>100 |
| (14) | 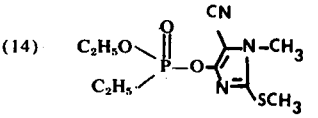 | 0.1<br>0.01 | 100<br>70 |
| (16) | 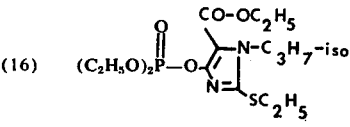 | 0.1 | 98 |

EXAMPLE 4

Critical concentration test/soil insects

Test insect: *Tenebrio molitor* larvae
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted in ppm (=mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness is 100% if all test insects had been killed and is 0% if exactly as many test insects were still alive as in the case of the untreated control.

The active compounds, amounts used and results can be seen from the table which follows:

Table 4
Critical concentration test/soil insects
(Tenebrio molitor larvae in the soil)

| Active compound | | Degree of destruction in % at an active compound concentration of 10 ppm |
|---|---|---|
| (D) | 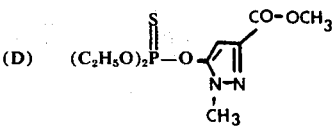 | 0 |
| (1) | 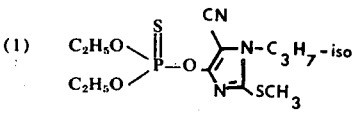 | 100 |

Table 4-continued

Critical concentration test/soil insects
(Tenebrio molitor larvae in the soil)

| Active compound | Degree of destruction in % at an active compound concentration of 10 ppm |
|---|---|
| (3) $(C_2H_5O)_2\overset{S}{P}-O-\underset{N}{\overset{CN}{\underset{SCH_3}{\bigg\langle}}}\!\!\!\!\!\!\!\!\!\!\!\!\!\!\!\!\!\!\!\!\!\!\!\!\!\!\!\!\!\!\!\!\!\!\!\!\!\!\!\!\!\!\!\!\overset{N-CH_3}{}$ | 100 |
| (5) $(CH_3O)_2\overset{S}{P}-O-\langle\overset{CN}{\underset{SCH_3}{N-C_3H_7-iso}}$ | 100 |
| (7) $\underset{C_2H_5}{\overset{C_2H_5O}{\diagdown}}\!\overset{S}{P}-O-\langle\overset{CN}{\underset{SCH_3}{N-C_3H_7-iso}}$ | 100 |
| (9) $(C_2H_5O)_2\overset{S}{P}-O-\langle\overset{CN}{\underset{SCH_3}{N-C_2H_5}}$ | 100 |
| (10) $\underset{C_2H_5O}{\overset{iso-C_3H_7-HN}{\diagdown}}\!\overset{S}{P}-O-\langle\overset{CN}{\underset{SCH_3}{N-C_2H_5}}$ | 100 |
| (12) $\underset{C_2H_5O}{\overset{iso-C_3H_7-HN}{\diagdown}}\!\overset{S}{P}-O-\langle\overset{CN}{\underset{SCH_3}{N-CH_3}}$ | 100 |
| (13) $(CH_3O)_2\overset{S}{P}-O-\langle\overset{CN}{\underset{SCH_3}{N-CH_3}}$ | 100 |
| (15) $(C_2H_5O)_2\overset{S}{P}-O-\langle\overset{CN}{\underset{SC_3H_7-iso}{N-C_3H_7-iso}}$ | 100 |
| (17) $(CH_3O)_2\overset{S}{P}-O-\langle\overset{CO-OC_2H_5}{\underset{SC_2H_5}{N-C_3H_7-iso}}$ | 100 |

EXAMPLE 5

Critical concentration test/soil insects

Test insect: *Phorbia antiqua* grubs
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was practically immaterial, the only decisive factor being the amount by weight of active compound per unit volume of soil, which is quoted in ppm (= mg/l). The soil was filled into pots and the pots were left to stand at room temperature.

After 24 hours the test insects were introduced into the treated soil and after a further 2 to 7 days the degree of effectiveness of the active compound was determined in % by counting the dead and live test insects. The degree of effectiveness is 100% if all test insects had been killed and is 0% if exactly as many test insects were still alive as in the case of the untreated control.

The active compounds, amounts used and results can be seen from the table which follows:

Table 5

Critical concentration test/soil insects
(*Phorbia antiqua* grubs in the soil)

| Active compound | Degree of destruction in % at an active compound concentration of 10 ppm |
|---|---|
| (C) $(CH_3O)_2\overset{S}{\overset{\|}{P}}-O-$ pyrazole with $CO-OCH_3$, $N-N$, $CH_3$ | 0 |
| (D) $(C_2H_5O)_2\overset{S}{\overset{\|}{P}}-O-$ pyrazole with $CO-OCH_3$, $N-N$, $CH_3$ | 0 |
| (1) $\begin{matrix}C_2H_5O\\C_2H_5O\end{matrix}\overset{S}{\overset{\|}{P}}-O-$ with $CN$, $N-C_3H_7$-iso, $SCH_3$ | 100 |
| (5) $(CH_3O)_2\overset{S}{\overset{\|}{P}}-O-$ with $CN$, $N-C_3H_7$-iso, $SCH_3$ | 100 |
| (7) $\begin{matrix}C_2H_5O\\C_2H_5\end{matrix}\overset{S}{\overset{\|}{P}}-O-$ with $CN$, $N-C_3H_7$-iso, $SCH_3$ | 100 |

Table 5-continued

Critical concentration test/soil insects
*(Phorbia antiqua grubs in the soil)*

| Active compound | Degree of destruction in % at an active compound concentration of 10 ppm |
|---|---|
| (10) iso-C$_3$H$_7$—HN—P(=S)(OC$_2$H$_5$)—O—C(CN)=N—C(SCH$_3$)=N—C$_2$H$_5$ | 100 |
| (12) iso-C$_3$H$_7$—HN—P(=S)(OC$_2$H$_5$)—O—C(CN)=N—C(SCH$_3$)=N—CH$_3$ | 100 |
| (17) (CH$_3$O)$_2$P(=S)—O—C(CO-OC$_2$H$_5$)=N—C(SC$_2$H$_5$)=N—C$_3$H$_7$-iso | 100 |
| (18) (C$_2$H$_5$O)$_2$P(=S)—O—C(CO-OC$_3$H$_7$-iso)=N—C(SCH$_3$)=N—C$_3$H$_7$-iso | 100 |

EXAMPLE 6

Critical concentration test/nematodes

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given in ppm, was decisive. The soil was filled into pots, lettuce was sown in and the pots were kept at a greenhouse temperature of 27°C.

After 4 weeks, the lettuce roots were examined for infestation with nematodes (root galls), and the degree of effectiveness of the active compound was determined as a percentage. The degree of effectiveness is 100% when infestation was completely avoided; it is 0% when the infestation was exactly the same as in the case of the control plants in untreated soil which had been infested in the same manner.

The active compounds, the amounts applied and the results can be seen from the following table:

Table 6

Critical concentration test/nematodes (*Meloidogyne incognita*)

| Active compound | Degree of destruction in % at an active compound concentration of 5 ppm |
|---|---|
| (C) $(CH_3O)_2\overset{S}{P}-O-$ [pyrazole with $CO-OCH_3$, $N-N$, $CH_3$] | 0 |
| (D) $(C_2H_5O)_2\overset{S}{P}-O-$ [pyrazole with $CO-OCH_3$, $N-N$, $CH_3$] | 0 |
| (1) $C_2H_5O\diagdown\overset{S}{\underset{}{P}}-O-$ [imidazole with $CN$, $N-C_3H_7\text{-iso}$, $SCH_3$], $C_2H_5O\diagup$ | 100 |
| (7) $C_2H_5O\diagdown\overset{S}{\underset{}{P}}-O-$ [imidazole with $CN$, $N-C_3H_7\text{-iso}$, $SCH_3$], $C_2H_5\diagup$ | 100 |
| (9) $(C_2H_5O)_2\overset{S}{P}-O-$ [imidazole with $CN$, $N-C_2H_5$, $SCH_3$] | 100 |
| (10) iso-$C_3H_7-HN\diagdown\overset{S}{\underset{}{P}}-O-$ [imidazole with $CN$, $N-C_2H_5$, $SCH_3$], $C_2H_5O\diagup$ | 100 |
| (12) iso-$C_3H_7-HN\diagdown\overset{S}{\underset{}{P}}-O-$ [imidazole with $CN$, $N-CH_3$, $SCH_3$], $C_2H_5O\diagup$ | 100 |

EXAMPLE 7

A. The imidazole derivatives of the formula (III) required as starting materials can be prepared, for example, as follows:

a)

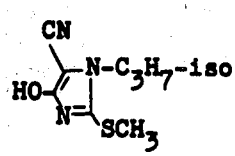

13 g of isopropylaminoacetonitrile acid ethyl ester isothiocyanate (obtained from potassium thiocyanate and chloroformic acid ethyl ester), of boiling point 55°C at 12 mm Hg, were added in the course of 10 minutes, at a temperature of −10° to 0°C, to a mixture of 10 g (0.1 mole) of isopropylaminoactonitrile (obtained from isopropylamine and hydroxyacetonitrile; see Cook and Cox, Soc. 1949, page 2,334), of boiling point 42°C at 1 mm Hg, in 200 ml of acetone. The mixture was stirred for a further 5 minutes at 0°C, 0.1 mole of sodium methylate solution was added at this temperature, and thereafter 12.6 g of dimethyl sulfate were added at 0° to 10°C. After stirring for a further 5 minutes at 5° − 10°C, a further 0.1 mole of a sodium methylate solution was added at 10° − 15°C. The reaction mixture was stirred for a further 15 minutes at this temperature and then evaporated, and the residue was dissolved in water. The solution was acidified with 6 g of glacial acetic acid and cooled, and the precipitate which had separated out was filtered off and dried. The precipitate could be recrystallized from acetonitrile. 14 g (71% of theory) of 1-isopropyl-2-methylthio-4-hydroxy-5-cyano-imidazole of melting point 196°–198°C were obtained.

The following could be prepared analogously from carbonic acid ethyl ester isothiocyanate:

1. With methylaminoacetonitrile of boiling point 40°C at 2 mm Hg

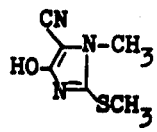

in a yield of 62% of theory, and with a melting point of 230°C.

2. With allylaminoacetonitrile of boiling point 54°C at 3 mm Hg

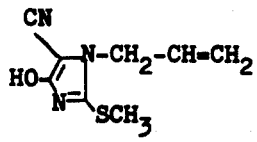

in a yield of 69% of theory and with a melting point of 163°C.

3. With ethylaminoacetonitrile of boiling point 68°C at 12 mm Hg

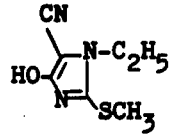

in a yield of 62% of theory and with a melting point of 176°C.

b$_1$. iso-C$_3$H$_7$—NH—CH$_2$—CO—OC$_2$H$_5$

Hydrogen chloride was passed into a solution of 49 g (0.5 mole) of isopropylaminoacetonitrile in 400 ml of ethanol at 20°–25°C, until saturation was reached. 18 g of water were then added at the stated temperature and the reaction mixture was stirred overnight and then warmed for 1 hour at a bath temperature of 80°C. The solids which had separated out were then filtered off, the filtrate was concentrated and the residue was poured into 100 ml of water. The mixture was extracted with methylene chloride, the organic phase was dried and the solvent was distilled off. The residue was distilled at 40°C and 1 mm Hg and 41 g (53% of theory) of isopropylaminoacetic acid ethyl ester having a refractive index n$_D^{20}$ of 1.4175 were thus obtained.

b$_2$.

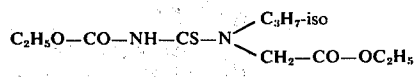

22 g of chlorocarbonic acid ethyl ester were added to 20 g (0.2 mole) of potassium thiocyanate in 250 ml of acetone at 50°–55°C and the mixture was stirred for a further 2 hours at 55°–60°C. 31 g of the product obtained under b$_1$) were then added at 20°–25°C, and the mixture was stirred for a further 2 hours and filtered. The solvent was evaporated off in vacuo and the residue was subjected to "slight distillation". 30 g (54% of theory) of the desired product were obtained.

b$_3$.

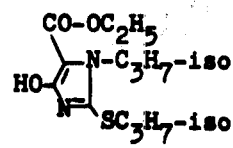

83 g (0.3 mole) of the product obtained under b$_2$) and 51 g of 2-iodopropane were added to 0.3 mole of a sodium ethylate solution and the mixture was stirred for 3 hours at 60°C. Thereafter a further 0.3 mole of a sodium ethylate solution were added dropwise and the mixture was boiled under reflux for 1 hour. It was then evaporated, the residue was dissolved in water and the solution was filtered through charcoal. 0.3 mole of pure concentrated hydrochloric acid was added to the aqueous phase and the precipitate was filtered off and dried on clay. 38 g (48% of theory) of 1-isopropyl-2-isopropylthio-4-hydroxy-5-carboethoxy-imidazole of melting point 97°–98°C were obtained.

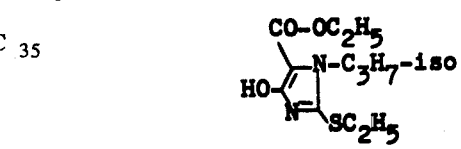

110 g of the product obtained under b$_2$) were added to 0.4 mole of a sodium ethylate solution and the mixture was stirred for one hour. 62 g of diethyl sulfate were then added dropwise at 30°–45°C, the whole was stirred for a further hour and thereafter a further 0.4 mole of a sodium ethylate solution was added. After boiling for one hour under reflux, the mixture was evaporated, the residue was dissolved in water and the solution was clarified with charcoal. 0.4 mole of concentrated hydrochloric acid was added to the solution and the precipitate which separated out was filtered off and dried on clay. 64 g (62% of theory) of 1-isopropyl-2-ethylthio-4-hydroxy-5-carboethoxyimidazole of melting point 82°–84°C were obtained.

The following could be prepared analogously:

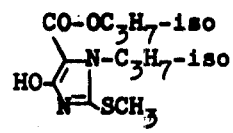

in a yield of 70% of theory and with a melting point of 95°C;

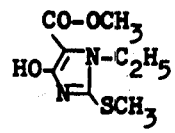

in a yield of 62% of theory and with a melting point of 145°C; and

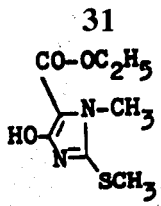

in a yield of 54% of theory and with a melting point of 120°C.

B.

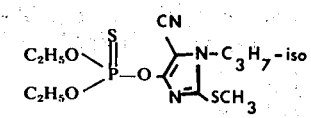

(1)

19 g of O,O-diethylthionophosphoric acid diester chloride were added to a mixture of 20 g (0.1 mole) of 1-isopropyl-2-methylthio-4-hydroxy-5-cyano-imidazole and 15 g of potassium carbonate in 200 ml of acetonitrile, whereupon the temperature of the reaction mixture rose to 32°C. The mixture was then heated to 70°–80°C for 3 hours while stirring after which it was poured into water. The whole was extracted by shaking with methylene chloride, the organic phase was washed and dried and the solvent was distilled off in vacuo. The residue was subjected to "slight distillation" and 29 g (83% of theory) of O,O-diethyl-O-[1-isopropyl-2-methylthio-5-cyano-imidazol(4)yl]-thionophosphoric acid ester having a refractive index $n_D^{22}$ of 1.5302 were thus obtained.

The following compounds can be prepared analogously:

| Compound No. | Structure | Physical data (refractive index, melting point) |
|---|---|---|
| (2) | ![structure] | $n_D^{22}$: 1.5322 |
| (3) | ![structure] | $n_D^{23}$: 1.5380 |
| (4) | ![structure] | $n_D^{23}$: 1.5358 |
| (5) | ![structure] | $n_D^{24}$: 1.5450 |
| (6) | ![structure] | 46°C |
| (7) | ![structure] | $n_D^{24}$: 1.5413 |
| (8) | ![structure] | 48°C |

-continued
| Compound No. | Structure | Physical data (refractive index, melting point) |
|---|---|---|
| (9) | 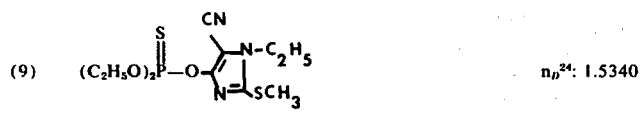 | $n_D^{24}$: 1.5340 |
| (10) | 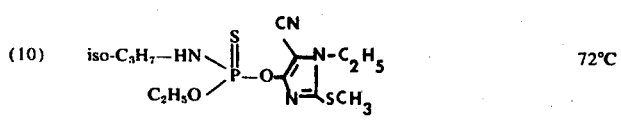 | 72°C |
| (11) | 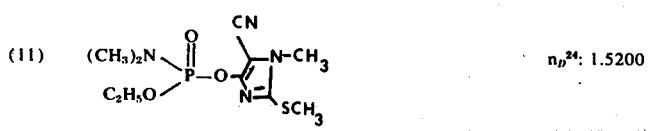 | $n_D^{24}$: 1.5200 |
| (12) | 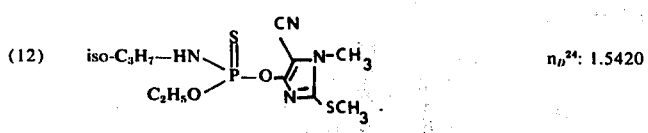 | $n_D^{24}$: 1.5420 |
| (13) | 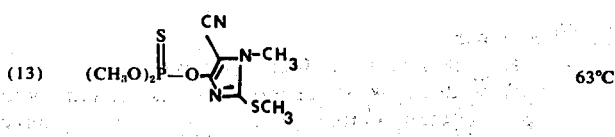 | 63°C |
| (14) | 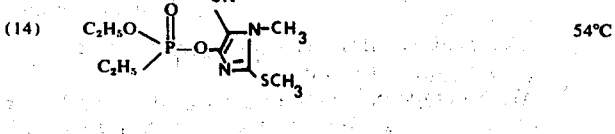 | 54°C |
| (15) | 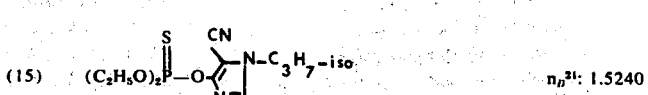 | $n_D^{21}$: 1.5240 |
| (16) | 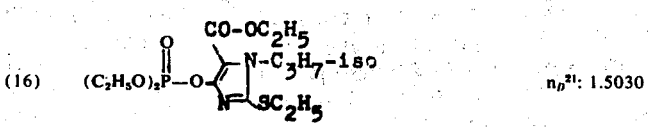 | $n_D^{21}$: 1.5030 |

| Compound No. | Structure | Physical data (refractive index, melting point) |
|---|---|---|
| (17) | 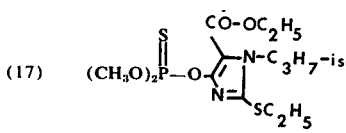 | $n_D^{21}$: 1.5321 |
| (18) | 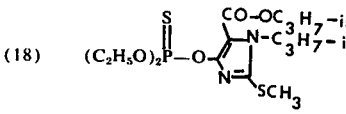 | $n_D^{23}$: 1.5190 |
| (19) | 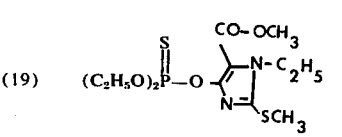 | 74°C |

Other compounds which can be similarly prepared include:

(20) 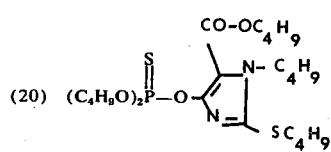

(21) 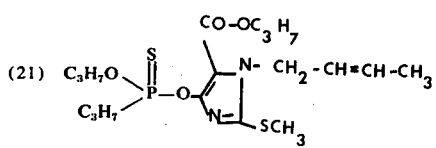

(22) 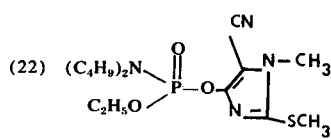

and the like.

It will be appreciated that the instant specification and examples are set forth by way of illustration and not limitation, and that various modifications and changes may be made without departing from the spirit and scope of the present invention.

What is claimed is:

1. An O-alkyl-O-[2-alkylthio-imidazol(4)yl]-(thiono)-phosphoric(phosphonic) acid ester or esteramide of the formula

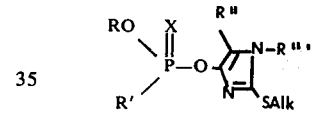

in which
R is alkyl with 1 to 6 carbon atoms,
R' is alkyl, alkoxy, or mono- or dialkylamino with 1 to 6 carbon atoms in each alkyl or alkoxy moiety,
R'' is cyano or carbalkoxy with 1 to 5 carbon atoms in the alkoxy chain,
R''' is alkyl or alkenyl each with up to 6 carbon atoms,
Alk is alkyl with 1 to 5 carbon atoms, and
X is oxygen or sulfur.

2. A compound according to claim 1, in which R is straight-chain or branched alkyl with 1 to 4 carbon atoms, R' is straight-chain or branched alkyl or alkoxy each with 1 to 4 carbon atoms, or monoalkylamino or dialkylamino with 1 to 5 carbon atoms per alkyl chain, R'' is cyano or carbalkoxy with 1 to 4 carbon atoms in the alkoxy radical, R''' is straight-chain or branched alkyl with 1 to 5 carbon atoms or alkenyl with 2 to 5 carbon atoms, and Alk is straight-chain or branched alkyl with 1 to 4 carbon atoms.

3. The compound according to claim 1 wherein such compound is O,O-diethyl-O-[1-methyl-2-methylthio-5-carbethoxy-imidazol(4)yl]-thionophosphoric acid ester of the formula

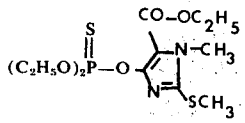

4. The compound according to claim 1 wherein such compound is O,O-diethyl-O-[5-cyano-2-methylthio-5-carbethoxy-imidazol(4)yl]-thionophosphoric acid ester of the formula

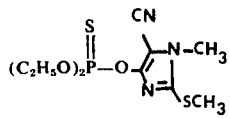

5. The compound according to claim 1 wherein such compound is O,O-diethyl-O-[1-allyl-2-methylthio-5-cyano-imidazol(4)yl]-thionophosphoric acid ester of the formula

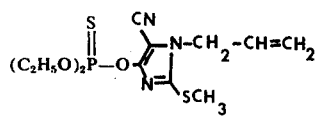

6. The compound according to claim 1 wherein such compound is O,O-dimethyl-O-[1-isopropyl-2-methylthio-5-cyano-imidazol(4)yl]-thionophosphoric acid ester of the formula

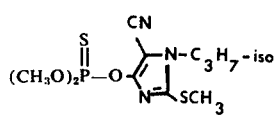

7. The compound according to claim 1 wherein such compound is O,O-dimethyl-O-[1-methyl-2-methylthio-5-cyano-imidazol(4)yl]-thionophosphoric acid ester of the formula

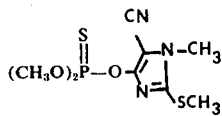

8. An insecticidal, acaricidal or nematicidal composition containing as active ingredient an insecticidally, acaricidally or nematicidally effective amount of a compound according to claim 1 in admixture with a diluent.

9. A method of combating insects, acarids or nematodes which comprises applying to the insects, acarids or nematodes or to a habitat thereof an insecticidally, acaricidally or nematicidally effective amount of a compound according to claim 1.

10. The method according to claim 9 in which said compound is
O,O-diethyl-O-[1-methyl-2-methylthio-5-carbethoxy-imidazol(4)yl]-thionophosphoric acid ester,
O,O-diethyl-O-[1-methyl-2-methylthio-5-cyano-imidazol(4)yl]-thionophosphoric acid ester,
O,O-diethyl-O-[1-allyl-2-methylthio-5-cyano-imidazol(4)yl]-thionophosphoric acid ester,
O,O-dimethyl-O-[1-isopropyl-2-methylthio-5-cyano-imidazol(4)yl]-thionophosphoric acid ester, or
O,O-dimethyl-O-[1-methyl-2-methylthio-5-cyano-imidazol(4)yl]-thionophosphoric acid ester.

* * * * *